United States Patent
Berndt et al.

(10) Patent No.: US 12,038,425 B2
(45) Date of Patent: Jul. 16, 2024

(54) PROCESS FOR ANALYZING DATA OF AT LEAST ONE MOBILE GAS MEASURING DEVICE AND OF A STATIONARY GAS MEASURING DEVICE AS WELL AS SYSTEM FOR MONITORING AT LEAST ONE GAS CONCENTRATION

(71) Applicant: Dräger Safety AG & Co. KGaA, Lübeck (DE)

(72) Inventors: Malte Berndt, Lübeck (DE); Christof Rodehorst, Lübeck (DE); Raphael Maas, Lübeck (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 226 days.

(21) Appl. No.: 17/683,829

(22) Filed: Mar. 1, 2022

(65) Prior Publication Data
US 2022/0291186 A1 Sep. 15, 2022

(30) Foreign Application Priority Data
Mar. 2, 2021 (DE) ...................... 10 2021 105 014.6

(51) Int. Cl.
*G01N 33/00* (2006.01)
*G08B 21/16* (2006.01)

(52) U.S. Cl.
CPC ..... *G01N 33/0075* (2013.01); *G01N 33/0006* (2013.01); *G08B 21/16* (2013.01)

(58) Field of Classification Search
CPC . G01N 33/0075; G01N 33/0006; G08B 21/16
USPC ....................................................... 340/628
See application file for complete search history.

(56) References Cited

U.S. PATENT DOCUMENTS

| | | | | |
|---|---|---|---|---|
| 10,271,116 | B2 * | 4/2019 | Davis | G01F 23/00 |
| 10,311,705 | B1 * | 6/2019 | Aljuaid | G05B 19/0428 |
| 10,962,437 | B1 * | 3/2021 | Nottrott | G01N 21/3504 |
| 11,519,809 | B2 * | 12/2022 | Ziolkowski | G01M 3/20 |

(Continued)

FOREIGN PATENT DOCUMENTS

| | | |
|---|---|---|
| EP | 1505385 B1 | 12/2010 |
| EP | 3343218 A1 | 7/2018 |

(Continued)

OTHER PUBLICATIONS

Australian Government IP Austrailia, Examination report No. 1 for your standard patent application, Application No. 2022201395, Feb. 2, 2023 (Year: 2023).*

*Primary Examiner* — Kerri L McNally
(74) *Attorney, Agent, or Firm* — McGlew and Tuttle, P.C.

(57) ABSTRACT

A process and a system analyze data of at least one mobile gas measuring device as well as of a stationary gas measuring device (3a, 3b). Data are generated by the mobile gas measuring device and by the stationary gas measuring device (3a, 3b) as a function of a gas concentration and are transmitted to a central data processing unit (1). Further, the data are supplemented with information in relation to a location of the data generation before, during or after the transmission. The processed data of the mobile gas measuring device and of the stationary gas measuring device (3a, 3b) are sent to a data analysis unit (2), in which a joint analysis of the processed data of the mobile gas measuring device and of the stationary gas measuring device (3a, 3b) is carried out for generating at least one result value.

20 Claims, 1 Drawing Sheet

(56) References Cited

U.S. PATENT DOCUMENTS

| | | | |
|---|---|---|---|
| 2015/0253300 A1 | 9/2015 | Zanfei et al. | |
| 2017/0102251 A1* | 4/2017 | Masson et al. | |
| 2017/0193790 A1* | 7/2017 | Cornwall | G01D 21/00 |
| 2018/0025611 A1* | 1/2018 | Johnson, Jr. | G06K 7/0095 |
| | | | 340/632 |
| 2018/0136180 A1 | 5/2018 | Chou | |
| 2019/0004023 A1 | 1/2019 | Kelly et al. | |
| 2019/0234924 A1* | 8/2019 | Anto | G01N 33/0063 |
| 2020/0249214 A1 | 8/2020 | Yoo et al. | |
| 2020/0378940 A1* | 12/2020 | Pariseau | F24F 11/30 |
| 2021/0033586 A1* | 2/2021 | Chadha | G01N 33/0065 |
| 2021/0318281 A1 | 10/2021 | Kraemer et al. | |

FOREIGN PATENT DOCUMENTS

| | | |
|---|---|---|
| GB | 2586540 A | 2/2021 |
| KR | 20170050244 A | 5/2017 |
| WO | 2021209116 A1 | 10/2021 |

\* cited by examiner

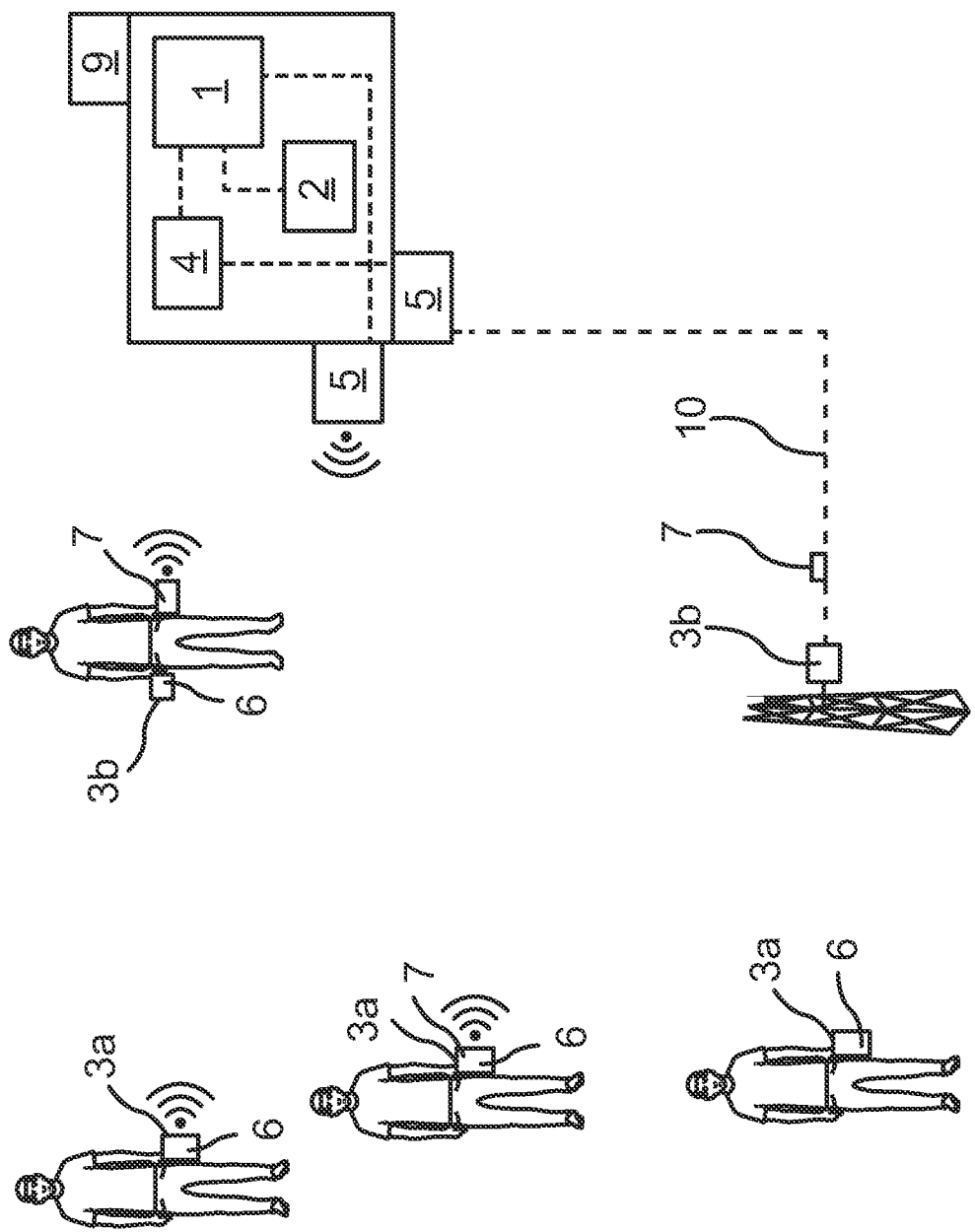

PROCESS FOR ANALYZING DATA OF AT LEAST ONE MOBILE GAS MEASURING DEVICE AND OF A STATIONARY GAS MEASURING DEVICE AS WELL AS SYSTEM FOR MONITORING AT LEAST ONE GAS CONCENTRATION

CROSS REFERENCE TO RELATED APPLICATIONS

This application claims the benefit of priority under 35 U.S.C. § 119 of German Application 10 2021 105 014.6, filed Mar. 2, 2021, the entire contents of which are incorporated herein by reference.

TECHNICAL FIELD

The present invention pertains to a process for analyzing data of at least one mobile gas measuring device and of a stationary gas measuring device as well as to a system for monitoring at least one concentration of a gas in a monitored area. Measured values are detected in the process described as well as in the system with mobile and stationary gas measuring devices and are transmitted to a central data processing unit, wherein the transmitted data are at least partially complemented with a piece of information concerning the detection time of the data.

TECHNICAL BACKGROUND

Mobile gas measuring devices are used for the protection of the people working in the working areas to monitor production sites, such as chemical plants or steel mills, refineries or mines, at which toxic, potentially explosive, combustible, low-oxygen or high-oxygen gas atmospheres may be formed. The mobile gas measuring devices have suitable sensors in order to detect the concentration of gases or gas mixtures, which are present in the respective work area or may occur at a hazardous concentration. Further, the mobile gas measuring devices have elements, which notify the device user and generate an alarm for the device user in case of a limit value violation.

Stationary gas measuring devices are used as well; they monitor above all special areas or plants of a production site, so that an alarm is generated as rapidly as possible and countermeasures can be initiated as soon as a toxic, combustible, potentially explosive atmosphere or a predefined gas component has been detected in the measurement area. The stationary gas measuring devices have for this purpose a suitably configured sensor. The continuously or intermittently generated measured data are forwarded for further processing to a central room, especially to a control room of a production site and are also recorded there at least partially for documentation purposes.

Contrary to the stationary gas measuring devices, mobile gas measuring devices are usually carried along by a measuring device user within the production site and are thus moved and they are used for personal protection or they are used for clearance measurements in crowded spaces. An essential feature of mobile gas measuring devices is that the user of the measuring device is informed and/or an alarm is generated for the device user if toxic gases or vapors reach a hazardous concentration, if a combustible or potentially explosive atmosphere has formed or if there is an oxygen deficiency or an excessively high oxygen content. Furthermore, the measured data generated are stored for at least a certain time in an internal memory of the device and are either read out at a station intended for this purpose at certain time cycles or, if the mobile measuring device is equipped for this, they are transmitted via a wireless data transmission connection to a central data processing unit of the control room of a production site.

Large quantities of data are usually generated and/or stored by means of the mobile as well as stationary gas measuring devices used at a production site, and they are not, however, available for a joint analysis. Possible synergies based on the joint analysis of the measured data provided by both mobile and stationary gas measuring devices are not consequently used. The data generated are often used only for documentation in the case of claims of damage or injury. By contrast, no further joint analysis is carried out.

A system for monitoring gas concentrations in a monitored area, in which a plurality of gas measuring devices are used, is known in this connection from US 2017/0193790 A1. The gas measuring devices transmit here the generated measured data to a central data processing unit. It is essential for the technical solution described that, on the one hand, the measurement intervals of a gas measuring device are reduced if detected measured values are coming close to a limit value and, on the other hand, additional gas measuring devices located in the vicinity are likewise activated or the measurement intervals are shortened in the case of these gas measuring devices as well. Even though both stationary and mobile gas measuring devices are used in this system for detecting gas concentrations as well, the respective generated data are not, however, fed for a joint processing, so that no possibly existing synergies can be used here, either.

A system for monitoring the concentration of gases in a monitored area by means of mobile and stationary gas measuring devices is likewise known from KR 2017-0050244 (A) as well. The monitoring system described is used for locating leaks and is characterized in that the gas measuring devices are connected in a branched network together with other technical components, e.g., control devices and control units, for data exchange. When a leak is detected by means of a mobile or stationary gas measuring device, it shall be possible after generation and transmission of measured data to a central data analysis unit to generate a control signal in an automated manner on the basis of the data analysis and to take the necessary actions, for example, to actuate a valve and to block off a pipe section. Thus, a plurality of data are generated and exchanged within a branched network, but there is again no joint use or no relationship between data is utilized.

SUMMARY

Based on the solutions known from the state of the art for monitoring a monitored area, especially a production site, in respect to gas concentrations occurring in different work areas by means of mobile and stationary gas measuring devices, a technical solution shall be proposed, with which measured values generated by the different gas measuring devices are used jointly. An improved monitoring and process control but, on the other hand, also the possibility of a reliable risk analysis and/or damage or injury claim investigation shall be made possible in this manner. It shall now be possible with comparatively simple means to use the measured data provided by stationary and mobile gas measuring devices in a suitable form for a joint data processing and data analysis in order to increase the accuracy of the measurement at a production site, on the one hand, and to be able to detect measuring errors as rapidly as possible, on the other hand. In particular, the possibility of a comparatively simple plausibility check in a monitoring system shall be implemented and the possibility of detecting and correcting measurement errors, measurement inaccuracies or measurement drifts of gas measuring devices being used possibly on the basis of the available data. In addition, it should be possible to take necessary actions rapidly and effectively and at the same time to ensure that no incorrect or superfluous interventions are made in a production process. Furthermore, a system configured according to the present invention shall increase the safety at a production site for the people working there, and the reliable monitoring of hard-to-access areas shall be ensured as well.

The above-described object is accomplished by means of a process in accordance with the invention as well as of a system for monitoring at least one concentration of a gas in accordance with the invention. Advantageous embodiments of the present invention are the subject of the dependent claims and will be explained in more detail in the following description partially with reference to figures.

The present invention pertains to a process for analyzing data of at least one mobile gas measuring device as well as of a stationary gas measuring device with the following steps:
  detection of data by the mobile gas measuring device and by the stationary gas measuring device, and
  transmission of the data from the mobile gas measuring device as well as from the stationary gas measuring device to a central data processing unit, which may also have a memory or may be coupled with such a memory, as well as at least partial processing of the data by supplementing (complementing) with information relating to a location of the site at which the data were detected.

The present invention is characterized in that the processed data of the mobile gas measuring device and of the stationary gas measuring device are sent to a data analysis unit, in which a joint analysis of the processed data of the mobile gas measuring device and of the stationary gas measuring device is carried out for generating at least one result value. The essential aspects of the process according to the present invention is that the data generated by at least one mobile gas measuring device as well as by at least one stationary gas measuring device, complemented (supplemented) by a piece of location-specific information, are transmitted to a central data processing unit, which may also contain a memory, and the data provided by different gas measuring devices are processed jointly at least partially such that the respective pieces of information contained are taken into consideration during the joint processing and/or a ratio of the different data in relation to one another is taken into consideration.

A result value is defined in this connection as a value which is generated during the joint analysis of the data of at least one mobile gas measuring device and at least one stationary gas measuring device and which is preferably compared to a threshold value or limit value or is analyzed taking a decision criterion into consideration, so that at least one suitable action can be taken based on the determined result value. Information relating to the location at which the generation of the corresponding data took place is taken into consideration during the joint analysis of the data provided by mobile and stationary gas measuring devices. It is pointed out in this connection that the location may also be a specified area.

The information on the location at which the respective data were generated and/or from which a data transmission took place is added from the respective gas measuring device, a gateway, via which a data transmission takes place at least partially, and/or by means of an additional device, for example, a device that analyzes a GPS signal, to the data before or during the transmission. Likewise, location information may be added by a separate external device and/or system, e.g., by the use of RFID technology. The location information is added in this case, for example, indirectly on the basis of the knowledge of the location of the device user or of a mobile gas measuring device. Furthermore, suitable location information may be present in an external system, because a corresponding input by the gas measuring device user or another person took place and/or because information on a gas measuring device user, which preferably contains a person-specific identification, e.g., a user ID, is linked in the system with information on the current location and/or at least suspected location and is made available for further data processing.

If an additional device is used to generate location information, the location information may also be added to the transmitted data after the transmission. The transmission of the data from the gas measuring device to a central data processing unit may take place generally either directly from the gas measuring device to the interface of the data processing unit, which interface is intended for this purpose, or it can be achieved via an additional transceiver unit, e.g., a mobile phone, which unit establishes an indirect data transmission connection between the gas measuring device and the interface of the central data processing unit.

A gateway, which enriches the transmitted data with the respective location information and/or with time information in relation to the data generation (data acquisition) and/or data transmission, may thus be arranged in the gas measuring device, in a transceiver unit or in the interface of the central data processing unit.

Based on the result value, at least one control signal is generated in a special embodiment of the present invention. According to this technical solution, the result value generated on the basis of the data provided by a mobile gas measuring device as well as by a stationary gas measuring device is used to generate a control signal and thus to take further actions in an automated manner. Further actions may comprise here both the notification of or and/or alarm generation for certain people, the activation of signal units at the production site and/or the specific intervention in production processes. In particular, a control signal may be generated on the basis of a generated result value and it is transmitted directly to an adjusting element, so that a device that can be actuated by the adjusting element, e.g., a valve, a heating or cooling element, a driving machine or processing machine and/or another adjusting mechanism, is actuated in a specific manner. A fan, a horn, a display and/or a relay, e.g., for interrupting an electric circuit, is especially preferably actuated in this case.

A possibility is thus created for intervening in a production or conveying process in an automated manner as a function of the result value generated or even for changing process parameters. The risk of development of a hazardous atmosphere can be minimized in this manner especially effectively, especially by taking suitable countermeasures in a specific manner in an affected production area and/or by setting up a classification of different production areas in respect to the existing hazard potential. Evacuation and/or shutdown of a production can thus be prevented in many cases. In addition, safety-related, assistance and/or rescue actions, which are based on the analysis of a comparatively large quantity of data, which are generated by gas measuring devices of different types distributed over a production site, can be taken especially rapidly and effectively.

Further, according to a special variant of the present invention, the information related to the location of the data generation (location of the data acquisition/creation), of the data transmission and/or of a time, especially of the data generation (data acquisition/creation) and/or data transmission, is added at least partially by the gas measuring device, which generates and/or transmits the respective data. Likewise, the information in relation to the location or the time of the data generation is added at least partially by the gateway, which is arranged in a gas measuring device, especially in a stationary gas measuring device, in a transceiver unit, for example, in a mobile phone, or in the interface of the central data processing unit. Especially in the case of the stationary gas measuring device, the location of the measurement is known and can be added in this manner to the transmitted data.

In an advantageous embodiment of the process according to the present invention, the transmitted data are stored at least intermediately, together with the information on the location and/or the time of the data generation or data transmission, in a central memory, which is arranged in the central data processing unit or can be connected to this at least from to time for data transmission. The data thus stored are available both for an immediate data processing and a later data processing, and it is possible to access these data later in time and/or repeatedly, especially for analysis purposes and for evaluations of claims of damage or injury. Data thus stored can be made available not only for different evaluations in relation to the production site at which they were generated, but also for other production sites, suppliers and/or customers.

As soon as a monitoring system of a production site is operated on the basis of the process according to the present invention for a certain time, data stored in this manner can further be used preferably for optimizing a safety concept, for carrying out risk analyses and/or for the specific planning and performance of device maintenance procedures. Furthermore, these data stored in a central memory may be used to train the control of the production plants at the production site on the basis of the stored data for optimization purposes.

According to another suitable embodiment of the present invention, at least one of the mobile or stationary gas measuring devices may have an internal memory, so that data generated by this device can be stored at least from time to time in the internal memory. If a mobile gas measuring device is a gas measuring device that has no device interface configured for wireless communication, i.e., wireless transmission especially of current data to the interface of the central data processing unit cannot take place, such an internal memory is used to store the generated measured data between two read-out times. The reading out of the data stored in the internal memory then takes place preferably with a suitable read-out device, e.g., during a maintenance or during a repair of the mobile gas measuring device.

In this connection at least one test station, calibration station and/or charging station may be provided with at least one mount for one of the mobile gas measuring devices, which mount is set up to calibrate a mobile gas measuring device, to supply an energy storage device of the mobile gas measuring device with electrical energy and/or to read the data stored in the memory of the mobile gas measuring device. The stored data may be both measured data and device-specific data that contain information on alarms that occurred during the past measurement time period and/or on errors that occurred during the past measurement time period. The data generated during the measurement time period are preferably transmitted with such a test, calibration and/or charging station to the interface of the central data processing unit. Such a test and calibration station, which is suitable for reading out and transmitting the data generated by a mobile gas measuring device, preferably has a gateway, which adds information on the location and the time of the data generation and/or of the data transmission to the read-out data prior to or during the transmission to the interface.

It is thus advantageous if the test, calibration and/or loading station used has an interface, via which data can be exchanged unidirectionally or bidirectionally with the interface of the data processing unit and when needed with a memory of the central data processing unit.

According to an especially preferred embodiment of the present invention, provisions are made for the data generated by a mobile and/or stationary gas measuring device to be transmitted to a central data processing unit, which is part of a control room of a production site and/or of a memory-programmable control. The transmitted data, which also contain information on the device, alarms that occurred during the measurement time period as well as errors that occurred, are preferably transmitted additionally to a central memory in order to be archived or made available for further use there. The data transmission takes place preferably via a gateway, which is arranged in the area of a measuring line, of a stationary gas measuring device, of a device holder and/or of a device interface or of an interface of the central data processing unit, and which adds at least one piece of information, especially a piece of information on the time and/or on the location of the data transmission, to the transmitted data. If the data transmission takes place from a stationary gas measuring device, the location of the stationary gas measuring device is likewise added to the transmitted data. As an alternative, the information on the location of the stationary gas measuring device may be added to the transmitted data on the basis of a device-specific identification of the data and on the knowledge of the current installation site of the stationary gas measuring device at a later time, for example, by the central data processing unit and especially by the data analysis unit.

The at least one mobile gas measuring device used transmits the generated data, preferably in a wireless manner (wirelessly), to an interface of the central data processing unit. In turn, in this connection the transmitted data may be stored at first at least intermediately in a memory of the central data processing unit. Especially in the case of devices that cannot establish a wireless data transmission connection to the interface of the central data processing unit, the data generated during a measurement time period may be stored at first in an internal memory. The data transmission takes place in this case at a later time by means of a suitable read-out device, which is capable of establishing an indirect data transmission connection between the mobile gas measuring device and the central data processing unit or a suitable interface of the data processing unit.

The information on the location of the data generation and/or of the data transmission is generated either by the mobile gas measuring device itself and is preferably stored with the data in the internal memory or it is added by a gateway, which may be arranged in the mobile gas measuring device, in a transceiver unit and/or in an interface of the central data processing unit. Generally, in this case as well, the data transmitted from a mobile gas measuring device to the central data processing unit may be supplemented with the information on the location of the data generation or of the data transmission on the basis of a corresponding identification only after the data transmission.

A large quantity of data are available when the process according to the present invention is used, and these data are generated by stationary and mobile gas measuring devices and they ensure a close monitoring of a production site in relation to properties of the atmospheres in different work areas, especially in respect to the presence of toxic, combustible or potentially explosive gas mixtures and/or of an oxygen deficiency. An especially reliable and close monitoring of a production site as well as an accurate data evaluation and analysis, above all, with high spatial resolution, are thus possible.

In a special embodiment, the process according to the present invention has been perfected such that a drift of at least one of the stationary gas measuring devices is detected during a measurement or during a measurement time period on the basis of the analysis of the processed data of the mobile and stationary gas measuring devices. This technical solution is thus based on the idea that by means of different mobile gas measuring devices, which are located at least from time to time in a measurement area that is also monitored by a stationary gas measuring device, measurements of the at least one mobile gas measuring device are used to check the measured data generated by the stationary gas measuring device for their plausibility. If a drift of the measured data, which are generated by the stationary gas measuring device, is detected, it is thus possible in a comparatively simple manner to take into consideration the corresponding error during the data analysis, especially to correct the measured data, or else to readjust the stationary gas measuring device or at least to correct an offset shift, or else to carry out maintenance on or replace the sensor in question.

Moreover, it is possible in an advantageous manner by means of the process according to the present invention to localize a leak in the area of the production site rapidly and with high accuracy on the basis of the analysis of the processed data of at least one mobile gas measuring device and of at least one stationary gas measuring device. Since both measured data of stationary gas measuring devices and of mobile gas measuring devices are used, and the generated measured data are analyzed jointly, are compared with one another and/or correlated with one another, it is possible to detect even comparatively minor leaks and thus to take the necessary measures rapidly and effectively.

Further, it is ensured by the joint processing of measured data, which are generated by stationary and mobile gas measuring devices, that false alarms are avoided or their number is at least reduced, because the respective measured data are subjected to a plausibility check during the joint data analysis and deviations or unusual measured values can be detected. Furthermore, according to a preferred embodiment of the present invention, a notification and/or a warning signal or alarm signal may be generated on the basis of the analysis of the processed data of the at least one mobile gas measuring device and of the at least one stationary gas measuring device in an automated manner. In this connection, the warning signal or alarm signal may be generated on the basis of the result value produced by the central data processing unit and is transmitted to at least one of the mobile gas measuring devices, to at least one additional gas measuring device located in the hazardous area, to a mobile phone, to a pager, to a computer and/or to an assistance service or rescue service. Such a technical solution is useful precisely when an error is detected in a mobile gas measuring device being used or when measurements by adjacent gas measuring devices suggest the existence of a hazardous situation.

For example, as soon as a stationary gas measuring device detects a toxic gas in a work area of a production site, which is not detected or cannot be detected by a mobile gas measuring device located in this work area, the user of the mobile gas measuring device may be notified or an alarm is generated for him. It is determined in such a case by the central data processing unit based on the joint processing, here especially comparison, of the data provided by the different gas measuring devices that differing data or data provided by only some of the gas measuring devices located there are present for a defined work area of the production site and a notification and/or alarm generation is carried out in the sense of an increased personal safety.

Furthermore, according to a special variant of the present invention at least one group of mobile gas measuring devices may be formed and the data forwarded, e.g., an alarm, which are transmitted from a stationary gas measuring device and which contain information, to at least one selected group of mobile gas measuring devices. This is especially advantageous when the location of the mobile gas measuring devices is not known or certain mobile gas measuring devices are always assigned to an area.

Another possibility is the assignment via a gateway, wherein an alarm is preferably automatically generated for all mobile gas measuring devices, which transmit data at least from time to time via the same gateway. A stationary measuring device can be assigned in this manner to a gateway, even if it is not connected to the corresponding gateway, and all mobile gas measuring devices connected to the gateway would generate an alarm as soon as the stationary gas measuring device generates alarm information.

In addition to a process, the present invention also pertains to a system for monitoring a concentration of a gas in a monitored area with at least one stationary gas measuring device and a mobile gas measuring device and with a central data processing unit, to which data, which were generated by the gas measuring devices, can be transmitted at least from time to time. The system according to the present invention is configured such that before, during or after the transmission to the central data processing unit, the data are processed by adding information about the location at which the data were generated and that a data analysis unit analyses the processed data of the mobile gas measuring device as well as of the stationary gas measuring device. The system according to the present invention is characterized in that the data analysis unit is set up to determine during a joint analysis and/or on the basis of a comparison of the processed data of the mobile gas measuring device and of the processed data of the stationary gas measuring device at least one result value, which is preferably used as a basis for a decision and/or as a trigger for further actions. In this connection, for example, the result value may be used as the basis for initiating suitable actions, e.g., an alarm generation or notification of needed assistants or rescue team members on the basis of a comparison with a limit value or threshold value and taking into consideration at least one decision criterion.

According to a preferred embodiment, the result value, which was generated, e.g., on the basis of a comparison of processed data of at least one mobile measuring device as well as of at least one stationary measuring device or by the joint use of data of at least one mobile measuring device as well as of at least one stationary measuring device in a calculation, can be used to generate in an automated manner a control signal, which is sent to a receiver in a wireless or wired manner. A control unit, which is configured to generate on the basis of the result value at least one control signal for actuating a valve, a fan, a heating or cooling element, a driving engine or processing machine, a display, a speaker, a siren, a fire extinguisher, an electrical shut-off device, an automatically closable door, a light, a mobile gas measuring device and/or an actuating drive, is therefore preferably provided.

Moreover, provisions are made in a special variant for at least one mobile gas measuring device to have an internal memory, in which the generated data, especially measured data or data that comprise information on alarms or device errors that occurred during the measurement time period, are stored intermediately at least until a later reading out by a suitable read-out device.

In another special embodiment of the present invention, a test and/or calibration station with at least one mount for at least one mobile gas measuring device is provided, which is set up to calibrate the mobile gas measuring device, to install a software or firmware update, to supply an energy storage device of the mobile gas measuring device with electrical energy, to read a memory of the mobile gas measuring device and/or to display a device parameter or a property of the device.

The test and/or calibration station preferably has a device interface, via which a unidirectional or bidirectional data transmission connection can be established to the central data processing unit, which preferably has a memory or is connected to a memory at least from time to time.

The above-described process as well as the described system for monitoring gas concentrations in a monitored area can preferably be used in industrial production, or manufacturing, for example, in the control room of a refinery, of a steel mill, of an industrial site for producing or processing chemicals, of a mine or a power plant and/or of a drilling or extraction platform.

The present invention will be explained below on the basis of special exemplary embodiments with reference to the figure without limitation of the general inventive idea. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:
FIG. 1 is a schematic view of a system for monitoring the concentration of at least one gas or gas mixture in a monitored area of a production site.

DESCRIPTION OF PREFERRED EMBODIMENTS

Referring to the drawings, FIG. 1 schematically shows a system for monitoring the concentration of at least one gas or gas mixture in a monitored area of a production site, in this case a refinery, at which different chemical media are processed, conveyed, produced and/or transferred, especially in the liquid or gaseous form. The system shown schematically is suitable in this case for monitoring the atmosphere in a plurality of work areas of the production site in respect to the presence of toxic gases or vapors, combustible or potentially explosive atmospheres or an oxygen deficiency. The monitoring system shown has stationary and mobile gas measuring devices 3a, 3b, with which the concentration of individual gases or gas mixtures is detected and corresponding data can be transmitted to a central data processing unit 1 of a control room of the production site.

Mobile and stationary gas measuring devices 3a, 3b are used for monitoring the production site shown schematically in FIG. 1. Mobile gas measuring devices 3a are used here mainly for the protection of the workers working in the work areas and they have suitable sensors in order to detect the concentration of gases or gas mixtures, which are present in the respective work area or may occur at a hazardous concentration. Further, the mobile gas measuring devices 3a have, on the one hand, elements that notify the device user in case of a limit value violation or generate an alarm for the device user and, on the other hand, a unit which makes possible at least from time to time the direct or indirect transmission of the generated data to a suitable interface of the central data processing unit 1.

The stationary gas measuring devices 3b monitor above all special areas or plants in the monitored area of the production site, so that an alarm is generated as rapidly as possible and countermeasures can be taken even before a toxic, combustible or potentially explosive atmosphere has been detected in the measurement area. The stationary gas measuring devices 3b have for this purpose a suitable sensor or a plurality of measuring heads with corresponding sensors. The measured data generated continuously or intermittently are forwarded for the further processing to a suitable interface 5 of the central data processing unit in the control room of the production site and are processed there immediately or after intermediate storage in a central memory 4.

According to the embodiment shown in FIG. 1, the data generated in the different gas measuring devices 3a, 3b are transmitted in a wireless or wired manner to a suitable interface 5 of the central data processing unit 1. The data are stored intermediately at least partially in a central memory 4 within the central data processing unit 1 and are analyzed either immediately or after an intermediate storage by means of a data analysis unit 2. The analysis of the data in the data analysis unit 2 is carried out such that both data from at least one mobile gas measuring device 3a and data from at least one stationary gas measuring device 3b are analyzed jointly, i.e., for example, compared, are used jointly for a calculation and/or correlated with one another. At least one result value, which depends on both the data provided by a mobile gas measuring device 3a and on the data provided by a stationary gas measuring device 3b, is determined now. In order to make it possible to carry out a suitable analysis, the data generated (data auired) by the gas measuring devices 3a, 3b are complemented with information on the location or at least on an area of the data generation carried out before, during or after their transmission to the central data processing unit 1 and still before the data analysis according to the present invention. After the data have been complemented with location-specific information, they are thus available as processed data for a joint analysis. It is possible by means of the result value generated in this manner to take the necessary actions rapidly, effectively and with high accuracy.

The suitable actions can be taken by the notification of or the generation of alarm for necessary maintenance, assistance or rescue staff members or by the automated generation of a control signal in a control unit 9, e.g., on the basis of a comparison of the result value with a limit value stored in the central data processing unit 1 or with a decision criterion. It is possible by means of the control signal, for example, to actuate a control unit in the area of a production plant such that a pipe section, in which a leak was detected, is blocked off. A plausibility check of the respective measured data provided by at least one stationary gas measuring device 3b and at least one mobile gas measuring device 3a is carried out during the generation of the result value, so that not only could the location of the leak be identified accurately, but it was also possible to largely rule out a false alarm and the taking of needless actions.

Furthermore, the joint analysis of the measured data provided by mobile and stationary gas measuring devices 3a, 3b takes place in the central data analysis unit 2 such that a special behavior of the device, which is triggered by, e.g., aging and time-dependent processes, for example, the drift of a sensor of a gas measuring device 3a, 3b, especially of a stationary gas measuring device 3b, is detected. It is advantageous in this connection that individual measurement areas are monitored at least from time to time both by at least one stationary gas measuring device 3b and also by a mobile gas measuring device 3a, which is carried along by a measuring device user, and the data transmitted to the data processing unit 1 and complemented by location information are analyzed jointly, and a connection is established between the information contents of the data provided by the different gas measuring devices 3.

Inaccuracies and sensor drifts of one of the measuring devices 3a, 3b, especially of a stationary gas measuring device 3b, can be detected by the comparison of the data provided both by a stationary and also at least one mobile gas measuring device 3b, 3a, especially if this takes place more frequently or even at regular intervals, and corresponding errors and/or drifts can be corrected or eliminated, for example, by taking a corresponding sensor drift into consideration during the data analysis or else by the corresponding sensor being replaced, recalibrated or by an offset correction being performed.

The measured data generated by a stationary gas measuring device 3b are usually transmitted via a measuring line 10 to a suitable interface 5 of the central data processing unit 1. Both the measured data but also data that contain information on device errors that occurred during the measurement time period or alarms that took place are transmitted not only to the data analysis unit 2, but additionally also to a central memory 4 and are stored there. The data stored in the central memory 4 are available for evaluations or analyses as well as for examinations of incidents, which are carried out at a later time.

In a gateway 7, which may be integrated in the stationary gas measuring device 3b, in the interface 5 of the central data processing unit 1 or in the measuring line 10, the transmitted data are supplemented with information on the time of the data transmission and on the location of the stationary gas measuring device 3b and hence with the location of the data generation. It is, however, possible, as an alternative, during the transmission of data from stationary gas measuring devices 3b to add the location information at a later time, because the position of the stationary gas measuring devices 3b is, as a rule, known and is present in the system, e.g., in a memory 4 connected to the central data processing unit 1. Since the data transmitted from the stationary gas measuring device 3b have a device-specific identification in this technical embodiment, the information on the location of the data generation may also be added in this manner to the transmitted data later in the central data processing unit 1.

The mobile gas measuring devices 3a used in the system according to FIG. 1 are usually connected to an interface 5 of the central data processing unit 1 via a wireless data transmission connection. The transmitted data may be processed immediately or only after an intermediate storage in a central memory 4 by the data analysis unit 2 configured according to the present invention in this case as well. It is generally advantageous if the data transmitted from a mobile gas measuring device 3a are stored in a central memory 4, so that these are also available for later evaluations or analyses. Moreover, the mobile gas measuring devices 3a have an internal memory 6, in which the respective data generated by the mobile gas measuring device 3a, i.e., both measured data and data that contain information on alarms or device errors that occurred during the measurement time period, are stored in a rolling manner. A rolling storage is defined in this connection such that as soon as the maximum storage capacity of the internal memory 6 has already been used up once, the oldest data of a memory 6 are always overwritten by the current data.

Depending on the configuration of a mobile gas measuring device 3a, the transmission of the data is carried out either by the gas measuring device 3a itself or else by means of a transceiver unit, for example, with a mobile phone, which establishes a data connection between the mobile gas measuring device 3a and the interface 5 of the central data processing unit 1. It is essential that depending on the technical configuration of the data transmission, either the gas measuring device 3a itself, the transceiver unit or the interface 5 of the central data processing unit 1 is set up such that information on the location of the data generation and preferably also information on the time of the data transmission are added to the transmitted data. Information on the location of the data generation (location of the data acquisition) may, moreover, be generated by means of an additional device or of an additional data generation system and it is added to the transmitted data in the central data processing unit. Likewise, the data generated by the mobile gas measuring device 3a, as processed data supplemented with information on the location at which the data were generated may be stored in the internal memory 6 before these data are transmitted to the central data processing unit 1 in a wireless manner or via a read-out device 8. The read-out device 8 is especially provided for the purpose of transmitting data to the central data processing unit 1, to which the mobile gas measuring device 3a is connected at least from time to time.

It is essential, in turn, for the technical solution described that data generated by stationary and mobile gas measuring devices 3a, 3b are transmitted to the central data processing unit 1, are stored here at least partially in a central memory 4 and are finally analyzed in a data analysis unit 2 such that the data generated by the different gas measuring devices 3a, 3b are used jointly for an analysis, and a correlation is established at least partially between the data provided by at least one stationary and a mobile gas measuring device 3b, 3a. It is possible due to such an analysis of the data generated by stationary and mobile gas measuring devices 3b, 3a, among other things, to subject the individual measurements to a plausibility check and/or to check the gas measuring devices 3a, 3b themselves to determine whether they function satisfactorily. If an analysis reveals that data provided by individual gas measuring devices 3a, 3b are not plausible when taking into consideration measured values that were recorded in the same measurement area by at least one other gas measuring device 3a, 3b, a corresponding piece of information can be generated and the gas measuring device 3a, 3b in question can be subjected to a testing. Likewise, as soon as a sensor drift is determined in a gas measuring device 3a, 3b on the basis of the comparison of the generated measured data with the measured data that were provided by at least one other gas measuring device 3a, 3b, this sensor drift will be taken into consideration in future measured data analyses. An offset correction of the sensor will be performed in an automated manner or the sensor in question will be replaced.

The monitoring system may also be configured such that during the joint analysis of measured data, which were provided by the mobile or stationary gas measuring devices 3a, 3b, the data analysis unit 1 determines a result value, which will then be compared to limit values or threshold values or specified decision criteria stored in the central data processing unit 1. Suitable actions can, in turn, be taken manually or in an automated manner on the basis of this comparison.

A suitable action may be defined in this connection both as the automated actuation of a control unit or of another device of a production plant of the production site, e.g., a fan, a relay or an electrical shut-off device, or else the output of information with which people are informed to take specific actions, for example, to replace a sensor or to actuate a control unit.

Likewise, based on a joint analysis of the data of at least one stationary mobile gas measuring device and one mobile gas measuring device 3b, 3a, a person who carries along a mobile gas measuring device 3b may be informed or an alarm may be generated for the person. Corresponding information or alarm generation may also take place when the respective mobile gas measuring device 3b has not generated itself an alarm signal, for example, because the relevant gas or gas mixture was not detected or could not be detected or because another device error is present. Reliable monitoring of a production site can be carried out with the system described, which makes possible a combined analysis of data that are provided by stationary and mobile gas measuring devices 3b, 3a.

Based on the combination of the data obtained in different manners, the accuracy of the data analysis is increased, the risk of false alarms is reduced, an additional monitoring of the different devices is made possible, and increased personal safety is achieved.

To detect the drift of a sensor, the processed data of a mobile gas measuring device 3a are preferably used in the data processing unit 1 to detect the drift of the sensor of a stationary gas measuring device 3b and, if possible, to correct it. The stationary measuring device 3b generates measured data at a fixed location, and these measured data are then analyzed for a predefined time period. An adjustment of the gas measuring device 3a is carried out first at the time of putting into operation or at defined time intervals during the operation. Further, at least one limit value, which shall not be overshot or undershot during a measurement in the measurement area, is stored for a gas concentration of at least one target gas. As soon as an inadmissible overshooting or undershooting of the limit value is detected, the measured data, which are generated by at least one mobile gas measuring device 3a which is present in the same measurement area at least from time to time, are also used for the data analysis. The measured data generated during the same time period for the same measurement area taking into consideration a tolerance of measured data generated by the mobile gas measuring device 3a are likewise used for a zero point determination. The values determined can now be compared and if a deviation that is greater than the variance to be expected is detected, a sensor drift of the stationary sensor is assumed. Depending on the value of the respective drift of the sensor in the stationary gas measuring device 3b, the drift is then corrected by calculation or maintenance is performed on the sensor or the sensor is replaced.

The greater the number of measured data available from a measurement area, which were recorded, for example, by different mobile and/or stationary gas measuring devices 3a, 3b in the measurement area and preferably over a longer time period, e.g., several days, the more accurately and more reliably can the drift of a gas measuring device 3a, 3b be determined. Employing techniques from the area of artificial intelligence and of machine elements, it is then possible to take into consideration the determined drift at the time of future adjustments, and the prediction of a drift and a change of a drift can be optimized by the use of a suitable algorithm. In order to achieve a precise prediction, the zero point determined by a mobile gas measuring device 3a is, furthermore, advantageously checked at regular intervals, e.g., in a test, calibration and/or charging station.

In case of a leak detection by means of the data provided by at least one stationary and at least one mobile gas measuring device 3b, 3a, the measured data of the stationary gas measuring device 3b are analyzed at first, and a slope of the measured curve is calculated. Likewise, the data generated in the same measurement area by a mobile gas measuring device 3a and transmitted to the central data processing unit 1 are analyzed. These data are also used to calculate the slope of a measured curve during the same measurement time period for the same location or for the same measurement area, taking the tolerance into account. If the slopes of the measured curves, which were determined during the evaluation of the data of the respective stationary and mobile measuring devices 3b, 3a, are correlated, a leak can be assumed. An alarm can thus be triggered at short notice and necessary actions can be taken, i.e., either assistants can be sent to the area of the leak or a control signal can be generated in an automated manner in order to block off the pipe section in which the leak is located.

Thus, the gas measuring devices 3a, 3b that are located in a specified production or measurement area are detected in an advantageous manner in a first step with the system described in order to subsequently determine a drift of a gas measuring device 3a, 3b and to take this into consideration for further measurements. Monitoring of the production or measurement area is then carried out, taking into consideration all the measured data generated by the different gas measuring devices 3a, 3b, and the individual measured data are subjected to plausibility checks. Additional parameters, e.g., process parameters and/or ambient parameters, e.g., the humidity of the air, air temperature, wind speed and wind direction, may be taken into consideration in the process during the monitoring of a production area or measurement area, and the generation of a control signal, which triggers a suitable action, may be based on them.

An especially precise monitoring can be achieved, for example, if the current dispersion of a target gas is used for the detection of a leak location. If, for example, a first mobile gas measuring device for H2S determines a gas concentration of 23 ppm, another device located 10 m to the east determines 35 ppm and a stationary gas measuring device located at the pipe carrying H2S detects 25 ppm, a leak location located between the pipe and the mobile gas measuring device located to the east is detected. Such a measurement can be further refined by taking the wind direction and the wind speed into consideration.

Furthermore, it is possible to use the data provided by at least one stationary and at least one mobile gas measuring device, 3b, 3a, for an early warning of people who are located in a hazardous area. Both the data recorded by a stationary and a mobile gas measuring device 3b, 3a, in a measurement area are available here to the central data processing unit 1. It is at first determined in the central data processing unit 1 when a mobile gas measuring device 3a is located in the vicinity of a stationary gas measuring device 3b. Different possibilities of an assignment are possible here. For example, it is possible to assign to one another measuring devices that are located in the same production area, for example, in a shop. An assignment may also be based on people, who carry along a mobile gas measuring device 3a each, especially if it is known that certain people, who are carrying along a mobile gas measuring device, are located in a known production area. A tolerance, which can be set in a needs-based manner and is set, for example, at 300 m, is taken, on the other hand, into consideration in case of an overlap of the location of a mobile gas measuring device 3a with the measurement area of a stationary gas measuring device 3b. The measured data that are provided by the stationary gas measuring device 3b are analyzed in the usual manner. As soon as a limit value violation is determined on the basis of these measured data, for example, because the measured values are above a limit value, the gas measuring device user, who is carrying along the mobile gas measuring device 3b located in the corresponding measurement area, is notified or an alarm is generated for the device user in an automated manner. An alarm can thus be generated in an automated manner for all mobile gas measuring devices 3a, which are located in the corresponding measurement area of the stationary gas measuring device 3b, whose measured data were used to detect a limit value violation, even when the mobile gas measuring device 3a carried along has not triggered any alarm.

As an alternative or in addition, the mobile gas measuring device 3a does not trigger an alarm in this case, but outputs information concerning the existing hazardous situation and the location of the stationary gas measuring device 3b, on the basis of the measured data of which a limit value violation was detected.

While specific embodiments of the invention have been shown and described in detail to illustrate the application of the principles of the invention, it will be understood that the invention may be embodied otherwise without departing from such principles.

LIST OF REFERENCE NUMBERS

1 Data processing unit
2 Data analysis unit
3a Mobile gas measuring device
3b Stationary gas measuring device
4 Central memory
5 Interface of the data processing unit
6 Internal memory
7 Gateway
8 Read-out device
9 Control unit
10 Measuring line

What is claimed is:

1. A process for analyzing data of at least one mobile gas measuring device as well as of a stationary gas measuring device, the process comprising the steps of:
generating data by the mobile gas measuring device and by the stationary gas measuring device as a function of a gas concentration;
transmitting the data from the mobile gas measuring device as well as from the stationary gas measuring device to a data processing unit and at least partially processing the data by supplementing the data with information in relation to a location of data generation;
sending the processed data of the mobile gas measuring device and stationary gas measuring device to a data analysis unit, in which a joint analysis of the processed data of the mobile gas measuring device and stationary gas measuring device takes place to generate at least one result value, the processed data comprising the location of data generation for the gas concentration from the mobile gas measuring device and the stationary gas measuring device, wherein a leak is located based on the joint analysis of the processed data of the mobile gas measuring device and the stationary gas measuring device.

2. A process in accordance with claim 1, further comprising generating a control signal, which generated based on the result value.

3. A process in accordance with claim 1, wherein the information in relation to the location of the data generation is added at least partially by the gas measuring device, which has generated the respective data.

4. A process in accordance with claim 1, wherein the information relating to the location of the data generation is added at least partially by a gateway.

5. A process in accordance with claim 1, wherein the information in relation to the location of the data generation is added at least partially by an external device and/or system.

6. A process in accordance with claim 1, wherein a drift of at least one stationary gas measuring device is detected during a measurement or over a time period based on the analysis of the processed data of the mobile gas measuring device and of the stationary gas measuring device.

7. A process in accordance with claim 1, wherein a warning signal is generated based on the analysis of the processed data of the mobile gas measuring device and of the stationary gas measuring device.

8. A process in accordance with claim 7, wherein the warning signal is transmitted to at least one of the mobile gas measuring devices.

9. A system for monitoring at least one concentration of a gas in a monitored area, the system comprising:
a mobile gas measuring device;
a stationary gas measuring device;
a processor configured to receive data generated by the gas measuring devices and processed by adding information in relation to a location at which the data were generated;
an analyzer configured to analyze the processed data and to determine at least one result value from the processed data of a mobile gas measuring device and from the processed data of a stationary gas measuring device based on a joint analysis of the processed data of the mobile gas measuring device and the stationary gas measuring device and/or based on a comparison of the processed data of the mobile gas measuring device and the stationary gas measuring device, the processed data comprising the location of data generation for the gas concentration from the mobile gas measuring device and the stationary gas measuring device, wherein the analyzer is configured to determine a location of a leak based on the joint analysis of the processed data of the mobile gas measuring device and the stationary gas measuring device.

10. A system in accordance with claim 9, further comprising a controller configured to generate, based on the result value, at least one control signal for actuating at least one of a valve, a heating or cooling element, a driving engine or a processing machine, a display, a speaker, a siren, a fire extinguisher, a mobile gas measuring device and an actuating drive.

11. A system in accordance with claim 9, further comprising a station comprising a mount for the mobile gas measuring device, wherein:
   the station is configured as at least one of a test station, a calibration station and a charging station; and
   the station is configured to calibrate the mobile gas measuring device, to supply an energy storage device of the mobile gas measuring device with electrical energy, to read out a memory of the mobile gas measuring device and/or to display device parameters.

12. A system in accordance with claim 11, wherein the station is a test and calibration station having an interface, via which data can be exchanged unidirectionally or bidirectionally with a central memory and/or with the analyzer, at least indirectly via the interface of the processor.

13. A process for monitoring at least one concentration of a gas, the process comprising:
   providing a system for monitoring at least one concentration of a gas in a monitored area in an industrial manufacturing plant, in a refinery and/or on a mining or drilling platform, wherein the system comprises:
      a mobile gas measuring device;
      a stationary gas measuring device;
      a data processing unit configured to receive data generated by the gas measuring devices and processed by adding information in relation to a location at which the data were generated; and
      a data analysis unit configured to analyze the processed data and to determine at least one result value from the processed data of a mobile gas measuring device and from the processed data of a stationary gas measuring device based on a joint analysis of the processed data of the mobile gas measuring device and the stationary gas measuring device and/or based on a comparison of the processed data of the mobile gas measuring device and the stationary gas measuring device, the processed data comprising the location of data generation for the gas concentration from the mobile gas measuring device and the stationary gas measuring device, wherein a leak is located based on an analysis of the processed data of the mobile gas measuring device and the stationary gas measuring device.

14. The process according to claim 13, wherein a measuring curve of the processed data of the mobile gas measuring device is determined and a measuring curve of the processed data of the stationary gas measuring device is determined.

15. The process according to claim 14, wherein a slope of the measuring curve of the process data of the mobile gas measuring device is determined and a slope of the measuring curve of the processed data of the stationary gas measuring device is determined.

16. The process according to claim 15, wherein the leak is located based on a comparison of the slope of the measuring curve of the processed data of the mobile gas measuring device and the slope of the measuring curve of the processed data of the stationary gas measuring device.

17. The process according to claim 13, wherein the processed data is stored in a central memory.

18. The system according to claim 9, wherein the analyzer is further configured to determine a measuring curve of the processed data of the mobile gas measuring device and to determine a measuring curve of the processed data of the stationary gas measuring device.

19. The system according to claim 18, wherein the analyzer is further configured to determine a slope of the measuring curve of the process data of the mobile gas measuring device and to determine a slope of the measuring curve of the processed data of the stationary gas measuring device.

20. The system according to claim 19, wherein the analyzer is configured to determine the location of the leak based on a comparison of the slope of the measuring curve of the processed data of the mobile gas measuring device and the slope of the measuring curve of the processed data of the stationary gas measuring device.

* * * * *